United States Patent
Raz et al.

(12) 
(10) Patent No.: US 6,323,040 B1
(45) Date of Patent: Nov. 27, 2001

(54) SYSTEM FOR BIOLOGICAL SPECIMEN PREPARATION

(76) Inventors: Ryan S. Raz, 46 Gwynne Ave., Toronto, Ontario (CA), M6K 2C3; Gordon Robertson, 15 Langley Ave., Toronto, Ontario (CA), M4K 1B4

( * ) Notice: Subject to any disclaimer, the term of this patent is extended or adjusted under 35 U.S.C. 154(b) by 0 days.

(21) Appl. No.: 09/503,905

(22) Filed: Feb. 15, 2000

(51) Int. Cl.⁷ .............................. G01N 1/00; G01N 33/48
(52) U.S. Cl. ............................ 436/174; 436/177; 436/46; 436/63; 435/40.51; 435/287.3; 435/288.5; 435/307.1
(58) Field of Search .................. 435/30, 40.5, 40.51, 435/6, 286.5, 287.3, 287.2, 288.5, 288.7, 307.1; 422/63, 68.1, 81, 82.05, 100, 101, 102; 436/46, 174, 175, 177; 73/863.23

(56) References Cited

U.S. PATENT DOCUMENTS

| | | |
|---|---|---|
| 4,758,238 * | 7/1988 | Sundblom et al. . |
| 5,595,707 * | 1/1997 | Copeland et al. . |
| 5,863,801 * | 1/1999 | Southgate et al. . |
| 5,942,700 | 8/1999 | Radcliffe et al. ................. 73/863.24 |
| 5,952,239 * | 9/1999 | Hayes et al. . |
| 6,073,482 * | 6/2000 | Moles . |
| 6,197,494 * | 3/2001 | Oberhardt . |

FOREIGN PATENT DOCUMENTS

| | | | |
|---|---|---|---|
| 07 43 524 A1 | 11/1996 | (EP) | ............................. G01N/35/00 |
| WO 98/53297 | 11/1998 | (WO) | ............................. G01N/1/28 |
| WO 98/10267 | 3/1998 | (WO) | ............................. G01N/15/14 |
| WO 99/60411 | 11/1999 | (WO) | ............................. G01N/35/00 |

* cited by examiner

Primary Examiner—William H. Beisner
(74) Attorney, Agent, or Firm—Ridout & Maybee

(57) ABSTRACT

A biological specimen preparation system for processing and depositing a portion of a biological specimen from a specimen vial onto a slide. The biological specimen preparation specimen includes a specimen processing unit and an external actuation unit. The specimen vial is connected to an input port on the specimen processing unit and the slide is coupled to an output port. A portion of the biological specimen is injected into the specimen processing unit and prepared by sequentially passing the biological specimen under the control of the external actuation unit through a number of specimen conditioning chambers and a specimen enrichment chamber in the specimen processing unit. The specimen is then deposited on the slide through the output port. To prevent sample to sample contamination, the specimen processing unit is manufactured as a disposable component using injection moulding techniques.

14 Claims, 4 Drawing Sheets

SYSTEM FOR BIOLOGICAL SPECIMEN PREPARATION

FIELD OF THE INVENTION

The present invention relates to a system for preparing a specimen from a cellular suspension of biological cells. In particular, the invention relates to apparatus and method for preparing a specimen comprising a uniform distribution of biological cells on a substrate surface.

BACKGROUND OF THE INVENTION

The collection or preservation of biological cells in fluid suspension is common in medicine and biology for the purpose of detecting disease. For example, naturally voided urine contains urothelial cells from the lining of the bladder. If the urothelial cells are separated from the urine and then placed on a substrate surface, such as a microscope slide, examination of the cells can determine the presence or absence of certain diseases. Another example is the PAP Smear Test which involves the artificial exfoliation of epithelial cells from the cervix of the uterus and the subsequent suspension of the exfoliated epithelial cells in a water/alcohol solution to preserve and protect the cells. If the epithelial cells are separated from the solution and then deposited on a microscope slide, examination of the cells can determine the presence or absence of pre-cancerous lesions on the cervix.

However, current techniques for the preparation of specimens from cellular suspensions are deficient since the cellular suspensions may contain debris and contaminants which can interfere with the examination of the desired ("target") cells. For instance, in the case of cervical epithelial specimen samples, the contaminants may include leukocytes, erythrocytes, bacteria and mucus. In addition, the typical specimen sample may contain several layers of cells and/or the cells may overlap one another, thereby rendering the detection of cell abnormalities difficult. Another reason is that, for the Pap test or indeed any other type of test requiring an exfoliation instrument, the technique of transferring the collected cells from the exfoliation instrument to the glass slide can be very inefficient. In some studies it has been shown that less than 20% of the collected sample is effectively transferred. By contrast, a liquid-based specimen allows, as a preliminary step, all of the collected cells to be rinsed or washed off of the exfoliation instrument into the collection fluid thereby improving specimen recovery and aiding in subsequent diagnostic accuracy.

With the exception of a membrane filter tube, all components used in the preparation of a biological specimen are reusable. This gives rise to the possibility of sample-to-sample contamination which in the context of medical applications cannot be ignored.

Accordingly, there remains a need for an apparatus and method for preparing specimens from cellular suspensions which enhances the ease and accuracy of evaluation of biological cells for abnormalities, and which eliminates the potential for sample-to-sample contamination.

SUMMARY OF THE INVENTION

According to the present invention, there is provided an apparatus and a method for preparing biological specimens from cellular suspensions which enhances the specimen recovery as well as the ease and accuracy of evaluation of biological target cells for abnormalities. In another aspect, the apparatus is designed to be disposable so as to eliminate the possibility of sample-to-sample contamination.

The biological specimen preparation system features an integrated processing unit or IPU. Advantageously, the integrated processing unit according to the present invention is inexpensive and easy to manufacture, using known injection-molded techniques. The design of the IPU also features the elimination of moving parts. The IPU is externally actuated wherein the motive force for the movement and distribution of fluids during the processing of the specimen is supplied externally.

In a first aspect, the present invention provides a biological specimen preparation system for depositing a portion of a biological specimen on a slide wherein the biological specimen is held in a vial, the biological specimen preparation system comprises: (a) a specimen processing unit having an input port for coupling to the vial containing the biological specimen and including a specimen conditioning chamber, and a specimen output port for depositing the conditioned specimen on the slide, an input channel connecting the input port to the specimen conditioning chamber and the specimen conditioning chamber having an output coupled to the specimen output port through an output channel, a first flow regulator for regulating the flow of the biological specimen through said input channel, and a second flow regulator for regulating the flow of the biological specimen through the output channel; (b) an actuation module for controlling the movement of the biological specimen in the specimen processing unit, the actuation module including an injector for injecting a portion of the biological specimen from said vial into the specimen conditioning chamber, a first actuator for actuating the first flow regulator and a second actuator for actuating the second flow regulator.

In another aspect, the present invention provides a method for preparing a biological specimen in a disposable specimen processing unit, the disposable specimen processing unit including an input port for coupling to a vial containing the biological specimen, and output port for coupling to a slide, the method comprising the steps of: (a) injecting a portion of the biological specimen from the vial to a first specimen conditioning chamber in the disposable specimen processing unit; (b) moving the biological specimen from the first specimen conditioning chamber to at least another specimen conditioning chamber in the disposable specimen processing unit for further conditioning; (c) moving the biological specimen form the last specimen conditioning chamber to a specimen enrichment chamber in the disposable specimen processing unit; (d) enriching the biological specimen in the specimen enrichment chamber by passing the biological specimen over a filter to remove contaminants from the biological specimen; (e) moving the enriched biological specimen from the specimen enrichment chamber to the output port for deposition on the slide.

BRIEF DESCRIPTION OF THE DRAWINGS

Reference will now be made to the accompanying drawings, which show by way of example, a preferred embodiment of the present invention, and in which.

DETAILED DESCRIPTION OF THE PREFERRED EMBODIMENT

Figure 1:
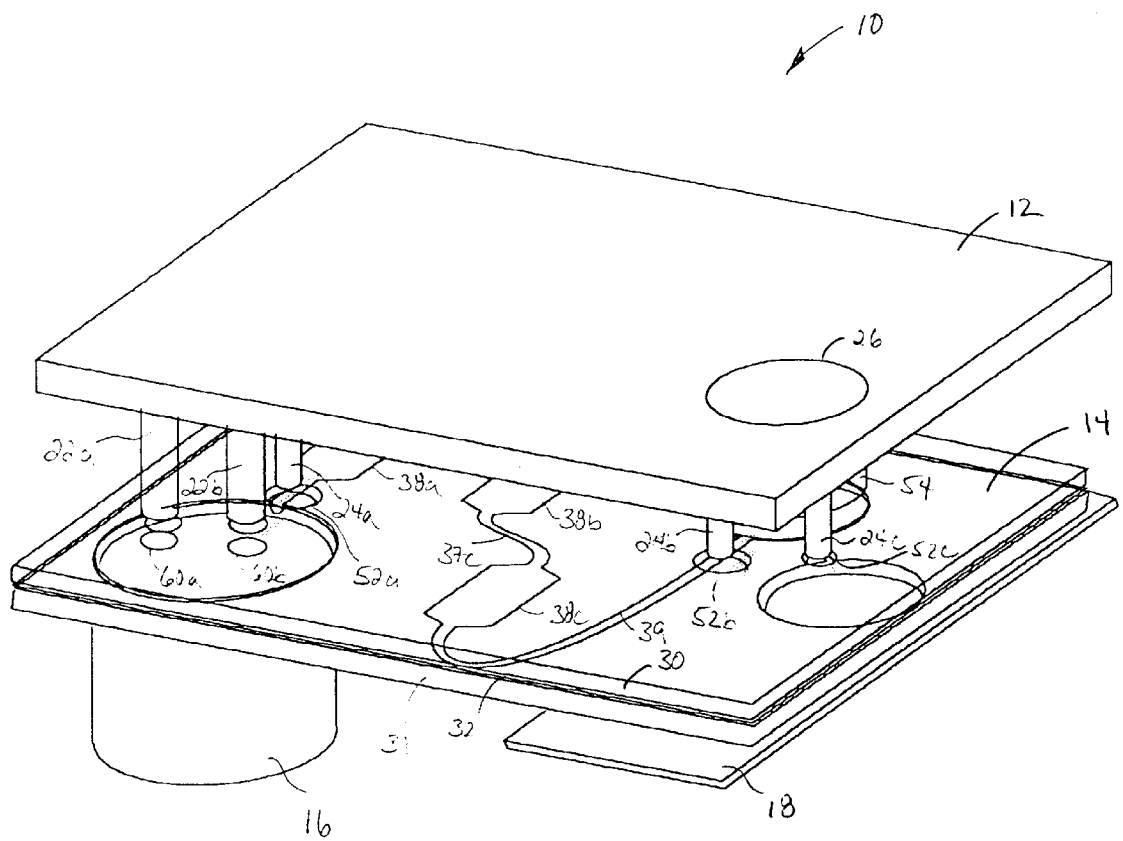
FIG. 1 shows in diagrammatic form a biological specimen preparation system according to the present invention.

Reference is first made to FIG. 1 which shows a biological specimen preparation system according to the present invention and denoted generally by reference 10. The specimen preparation system 10 provides an apparatus for extracting a portion of a biological sample or specimen contained in a specimen vial and depositing the biological sample on microscope slide for further analysis.

Figure 2:
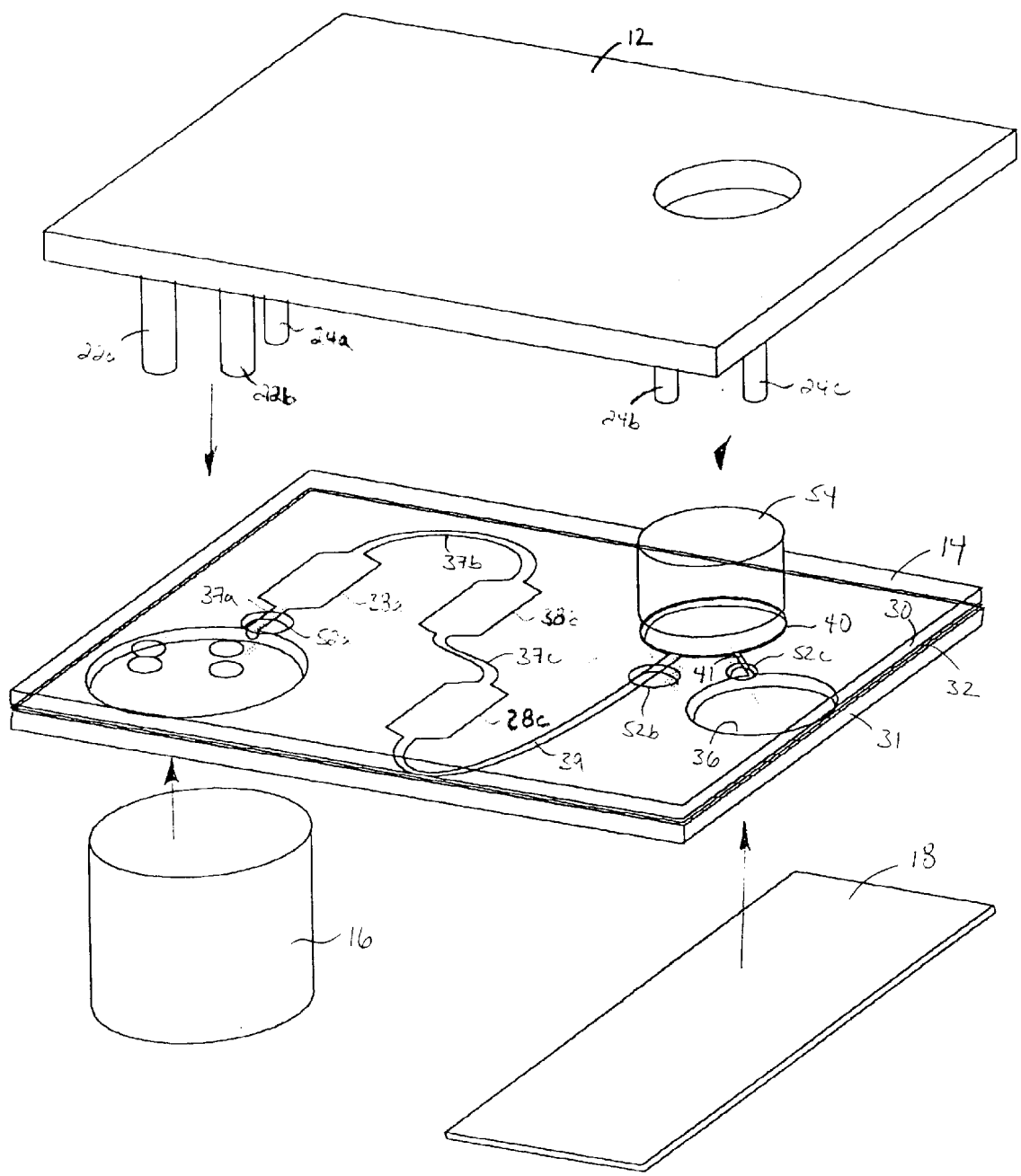
FIG. 2 shows the specimen preparation system of FIG. 1 in an exploded view.

As shown in FIG. 1, the integrated specimen processing system 10 comprises an external actuation module (or EAS) 12, an integrated processing unit (or IPU) 14, a specimen vial 16 and a slide 18. The integrated processing system 10 is shown in an exploded view in FIG. 2. In the drawings like reference numerals indicate like elements.

As will be described in more detail below, the integrated processing unit or IPU 14 comprises air and fluid couplings which provide both motive force for moving the biological specimen and the capability for diluting the sample before placement on the microscope slide 18. A portion of the biological specimen is extracted from the specimen vial 16 and moved through a series of specimen conditioning chambers and a specimen enrichment chamber before being deposited on the microscope slide 18. As will also be described, the integrated processing unit (or IPU) 14 includes a series of pinch valves which control the fluid distribution within the IPU 14. The pinch valves are activated by the external actuation system 12.

Referring to FIG. 1, the specimen vial 16 and the microscope slide 18 are coupled to the integrated processing unit or IPU 14. The IPU 14 is then mated to the external actuation module 12 to form the biological specimen preparation system 10.

Figure 3:
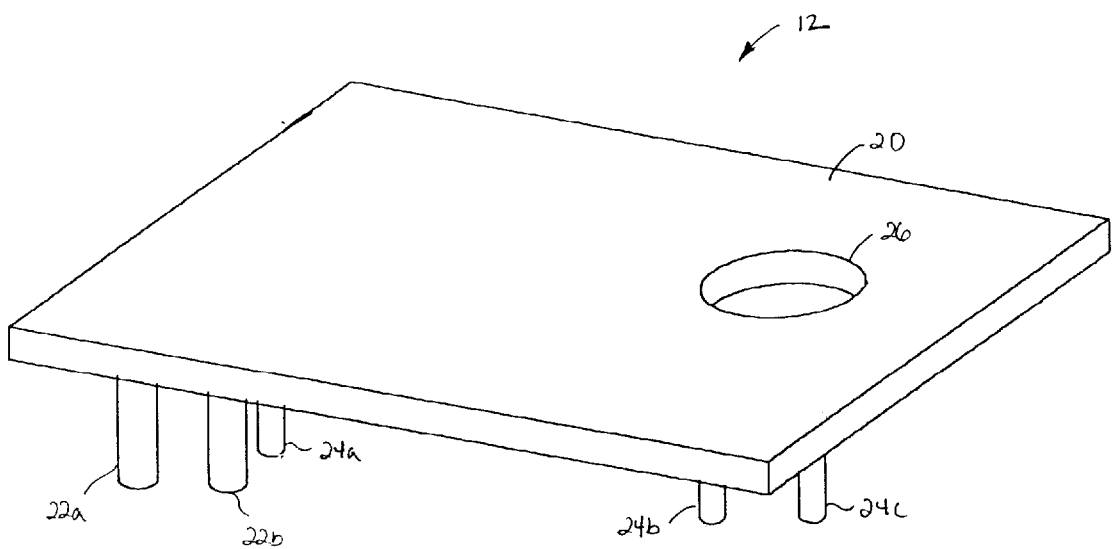
FIG. 3 shows in more detail the external actuation unit for the specimen preparation system of FIG. 1.

Reference is made to FIG. 3 which shows the external actuation system module (or EAS) 12. The external actuation system module 12 is designed to be a reusable component in the biological specimen preparation system 10 according to the present invention. The external actuation system module 12 comprises a support member 20, fluid couplers 22, push rods 24, and a measurement opening 26. The external actuation module 12 is coupled to the integrated processing unit (or IPU) 14. The fluid couplers 22, shown individually as 22a and 22b, supply differential air pressure streams which provide a motive force for moving a portion of the biological specimen from the specimen vial 16 into the integrated processing unit 16. The push rods 24, shown individually as 24a, 24b, 24c, control the passage of the biological specimen through the specimen conditioning chambers 38, the specimen enrichment chamber 40, and the specimen settling chamber 36 as will be described in more detail below with reference to FIG. 4. The measurement opening 26 provides a window for monitoring the flow of the fluid containing the specimen during the preparation process in the IPU 14. The measurement opening 26 is also used for measuring the density of the specimen.

Figure 4:
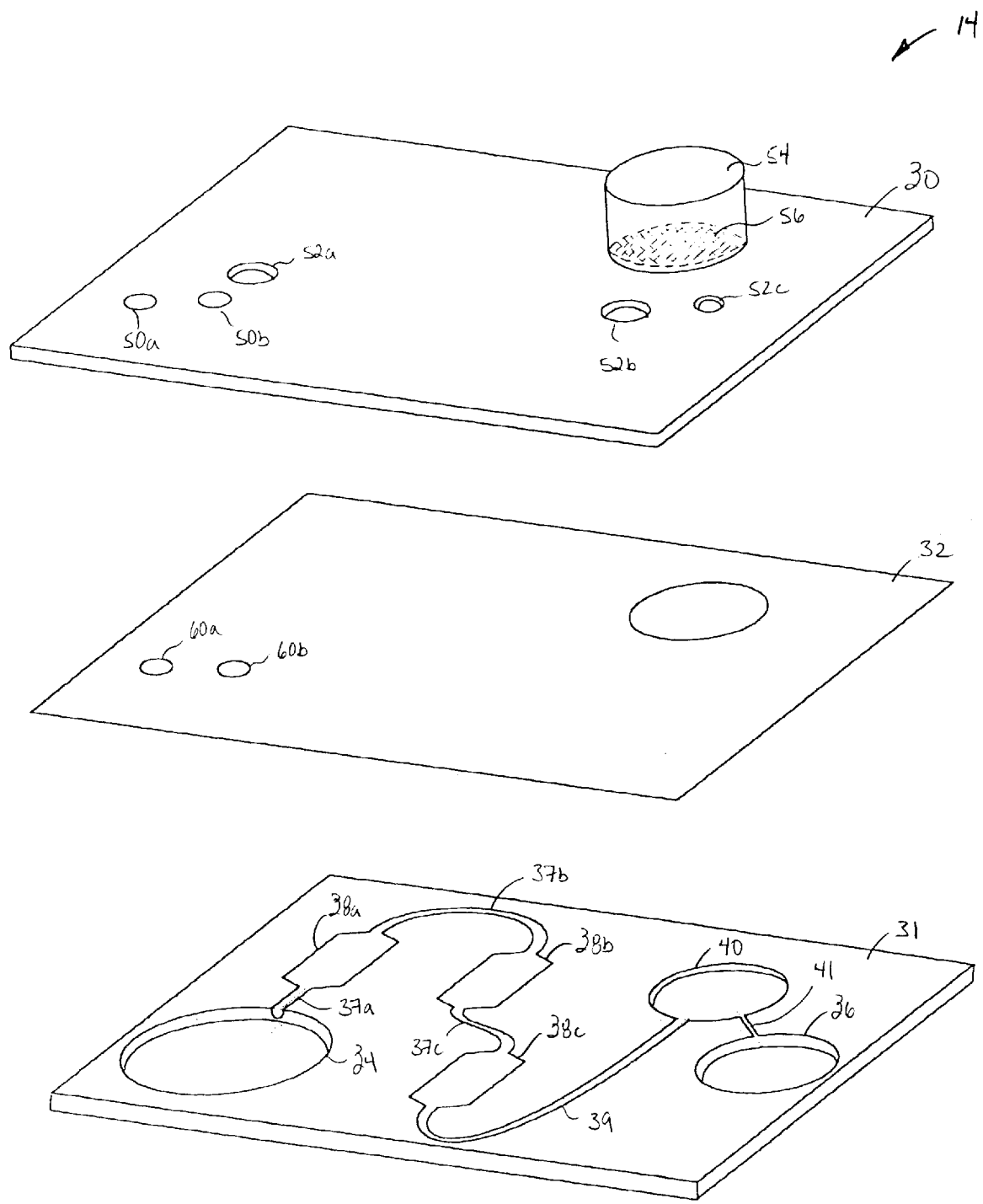
FIG. 4 shows in more detail the integrated processing unit for the specimen preparation system of FIG. 1.

Reference is next made to FIG. 4 which shows the integrated processing unit 14 in more detail. As shown, the integrated processing unit 14 comprises a top member 30, a bottom member 31, and a flexible sheet member 32.

The flexible sheet member 32 is sandwiched between the top 30 and bottom 31 members. The bottom member 31 includes a specimen vial port 34 for coupling the specimen vial 16. The bottom member 31 also includes a settling chamber 36 for depositing the processed biological specimen on the microscope slide 18. As shown in FIG. 4, the integrated processing unit 14 includes a series of specimen conditioning chambers 38, shown individually as 38a, 38b and 38c, and a specimen enrichment chamber 40. The specimen conditioning chambers 38 provide a volumetric area for agitating and settling the biological specimen and also for diluting the specimen. The first specimen conditioning chamber 38a receives the initial portion of the biological specimen which is injected from the specimen vial 16. The first specimen conditioning chamber 38a is coupled to the specimen vial port 34 through a channel 37a. The biological specimen moves between the first specimen conditioning chamber 38a and the second specimen conditioning chamber 38b via a channel 37b. Similarly, the processed biological specimen moves between the second specimen conditioning chamber 38b and the third specimen conditioning chamber 38c via channel 37c. The output of the third specimen conditioning chamber 38c is coupled to the specimen enrichment chamber 40 via channel 39. The output of the specimen enrichment chamber 40 is coupled to the settling chamber 36 by a channel 41. Preferably, the specimen conditioning chambers 38, the specimen enrichment chamber 40, the specimen settling chamber 36, and the respective channels 37, 39, 41 are formed into the bottom member 31 of the integrated processing unit 14.

The loading of a portion of the biological sample from the specimen vial 16 into the first specimen conditioning chamber 38a and the subsequent movement of the biological specimen between the conditioning chambers 38 and the enrichment chamber 40 and the settling chamber 36 is achieved by a sequential actuation of the fluid couplers 22 and the push rods 24 to deflect the flexible sheet member 32. Preferably, the sequential activation is performed under the control of a programmable microprocessor-based interface.

As shown in FIG. 4, the top member 30 includes openings 50, shown individually as 50a and 50b, for the respective fluid couplers 22a and 22b (FIG. 3) on the external actuation module 12. The flexible sheet member 32 also includes respective openings 60, shown individually as 60a and 60b, which register with the openings 50a and 50b and allow the fluid couplers 22a and 22b to communicate with the specimen vial port 34 on the bottom member 31 of the integrated processing unit 14. The top member 30 also includes openings 52, shown individually as 52a, 52b and 52c, for the respective push rods 24a, 24b and 24c (FIG. 3) on the external actuation module 12. The openings 52 allow the push rods 52 to move up and down against the flexible sheet member 32 and deflect regions of the sheet member 32. The opening 52a is associated with the channel 37a which couples the specimen vial port 34 to the input of the first specimen conditioning chamber 38a and deflection of the flexible sheet member over the channel 37a by the push rod 24a controls the injection of the biological specimen from the specimen vial 16 into the first specimen conditioning chamber 38a. The second opening 52b is associated with the channel 39 which couples the input of the specimen enrichment chamber 40 to the output of the last specimen conditioning chamber 38c. Deflection of flexible sheet member 31 against the channel 39 by the push rod 24b controls the passage of the biological specimen from the conditioning chamber 38c to the enrichment chamber 40. The third opening 52c is associated with the channel 41 which connects the output of the enrichment chamber 40 to the input of the specimen settling chamber 36. Deflection of the flexible sheet member 31 by movement of the push rod 24c through the opening 52c controls the passage of the biological specimen from the specimen enrichment chamber 40 into the specimen settling chamber 36 and onto the microscope slide 18. The push rods 24 are sequentially actuated to move the biological specimen between the specimen conditioning chambers 38, the enrichment chamber 40 and the settling chamber 36.

As shown in FIG. 4, the top member 30 of the integrated processing unit 14 also includes a specimen enrichment chamber 54 having a membrane filter. The specimen enrichment chamber 54 is coupled to the specimen enrichment port 40 and provides a mechanism for enriching the biological specimen. The specimen enrichment chamber 54 includes a disc-shaped membrane filter 56 (shown in broken outline inside the chamber 54). The membrane filter 56 registers with the specimen enrichment port 40 and includes a plurality of ports. The ports are larger than the debris, mucus and other contaminants which may be present in the fluid sample containing the biological specimen, but smaller than the biological target cells, so that the debris, mucus and contaminants are allowed to pass through the membrane filter 56, while the biological target cells are retained in specimen enrichment port 40. The biological specimen is enriched by increasing the number of biological target cells through the removal of the debris, mucus and contaminants. In one embodiment, the specimen enrichment chamber 54 is made from a transparent material so that a specimen density measurement can be made by the EAS 12. In another embodiment, the specimen density is pre-determined through an optical turbidity measurement which is taken with the biological specimen in the specimen vial 16. Once sufficient specimen density is reached, the push rod 24c is released to open the output channel 41 and allow the specimen to move from the specimen enrichment chamber 54 to the settling chamber 36 and onto the slide 18.

The biological specimen contained in the specimen vial 16 comprises a preservation fluid (e.g. water and alcohol, or other known anti-microbial compounds) and biological cells obtained through an artificial cellular exfoliation procedure. For example, the biological cells may comprise uterine cervical epithelial cells obtained through the well-known PAP smear. The preservation fluid preserves the exfoliated cells until a specimen can be processed and deposited on the microscope slide 18.

The biological target cells moved to the specimen settling chamber 36 from the specimen enrichment chamber 40 via the channel 41 are allowed to settle onto the upper substrate surface of the microscope slide 18 under the influence of gravity. Since the biological target cells are substantially uniformly distributed over the surface of the membrane filter 56, the biological target cells will also be substantially uniformly distributed over the upper substrate of the microscope slide 18. Preferably, the upper substrate of the slide 18 is provided with a polymer layer, such as poly-L-lysine, which improves the strength of attachment between the upper substrate surface of the slide 18 and the biological target cells received from the specimen enrichment chamber 40. Advantageously, the finished microscope slide 18 comprises a single layer of biological target cells which do not overlap and are ready for subsequent preparation steps, such as staining according to the well-known Papanicolaou test, cover-slipping, etc.

In operation, the external activation module 14 provides a differential air pressure through the fluid couplers 22a, 22b to place the biological specimen in the specimen vial 16 into suspension and to drive it into the first specimen conditioning chamber 38a via the input channel 37a. The push rod 24a controls injection of the biological specimen into the first specimen conditioning chamber 38a by pinching and opening the input channel 37a. The biological specimen is then directed through the other specimen conditioning chambers 38b and 38c. Each specimen chamber 38 provides a volumetric area for controlling the flow of the specimen through the operation of the fluid couplers 22a, 22b and the push rod 24a. After the third specimen conditioning chamber 38c, the biological specimen is directed to the specimen enrichment chamber 54 through the channel 39 which is pinched and closed by the operation of the push rod 24b. At the specimen enrichment chamber 54, the specimen is enriched through a succession of fluid motions (under the control of the fluid couplers 22a, 22b) which drive the specimen across the membrane filter 56. Since the openings in the membrane filter 56 are larger that the debris and mucus present in the fluid sample containing the specimen, the debris and mucus pass through the filter 56, whereas the larger biological target cells are retained in the specimen enrichment port 40. The biological specimen is enriched by increasing the number of fluid motions to increase the debris, mucus and other contaminants from the fluid sample. Before the specimen is passed to the settling chamber 36 for deposition on the slide 18, the specimen density needs to be determined to ensure the density is sufficient. The density of specimen may be measured by the external actuation system module 12 through the specimen enrichment chamber 54. In another embodiment, the specimen density is determined by making an optical turbidity measurement of the biological specimen in the specimen vial 16. The optical turbidity of the specimen is related to the density of cells in the specimen. By knowing the optical turbidity, a specified volume of the specimen is measured out from the specimen vial 16 to provide a specimen with the required cell density. Once the required cell density for the specimen is attained, the push rod 24c is actuated to open the channel 41 and allow the specimen to flow into the settling chamber 36 and onto the surface of the slide 18.

The present invention may be embodied in other specific forms without departing from the spirit or essential characteristics thereof. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A biological specimen preparation system for depositing a portion of a biological specimen on a slide wherein said biological specimen is held in a vial, said biological specimen preparation system comprises:

(a) a specimen processing unit having an input port for coupling to the vial containing said biological specimen and including a specimen conditioning chamber, and a specimen output port for depositing said conditioned specimen on the slide, an input channel connecting said input port to said specimen conditioning chamber and said specimen conditioning chamber having an output coupled to said specimen output port through an output channel, a first flow regulator for regulating the flow of said biological specimen through said input channel, and a second flow regulator for regulating the flow of said biological specimen through said output channel;

(b) an actuation module for controlling the movement of said biological specimen in said specimen processing unit, said actuation module including an injector for injecting a portion of said biological specimen from said vial into said specimen conditioning chamber, a first actuator for actuating said first flow regulator and a second actuator for actuating said second flow regulator.

2. The biological specimen preparation system as claimed in claim 1, wherein said processing unit includes a specimen enrichment chamber, said specimen enrichment chamber having an input coupled to the output of said specimen conditioning chamber through a connecting channel, and an output coupled to said output channel, and said processing unit including a third flow regulator for regulating the flow of said biological specimen through said connecting channel, said specimen enrichment chamber including a filter for removing contaminants from said biological specimen, and said actuation module including a third actuator for actuating said third flow regulator.

3. The biological specimen preparation system as claimed in claim 2, wherein said specimen conditioning chamber includes means for determining a cell density measurement for said biological specimen.

4. The biological specimen preparation system as claimed in claim 1, further including means for taking an optical turbidity measurement.

5. The biological specimen preparation system as claimed in claim 1, wherein said specimen processing unit comprises a base member, a top member, and a flexible member disposed between said base member and said top member, said specimen conditioning chamber and said input channel and said output channel being formed in said base member.

6. The biological specimen preparation system as claimed in claim 5, wherein said first actuator includes a push rod and said second actuator includes a second push rod and wherein said first flow regulator comprises an aperture in said top member for receiving a push rod, said aperture being in communication with a section of said input channel and providing for said push rod to deflect a portion of said flexible member over said input channel and thereby close off said input channel, and said second flow regulator comprising a second aperture in said top member for receiving a second push rod, said second aperture being in communication with a section of said output channel and providing for said second push rod to deflect a portion of said flexible member over said output channel and thereby close off said output channel.

7. The biological specimen preparation system as claimed in claim 6, wherein said specimen processing unit includes a specimen enrichment chamber, said specimen enrichment chamber having an input coupled to the output of said specimen conditioning chamber through a connecting channel, and an output coupled to said output channel, and said specimen processing unit including a third flow regulator for regulating the flow of said biological specimen through said connecting channel, said specimen enrichment chamber including a filter for removing contaminants from said biological specimen, and said actuation unit includes a third actuator for actuating said third flow regulator.

8. The biological specimen preparation system as claimed in claim 7, wherein said third actuator comprises a third push rod and said third flow regulator comprises an aperture in said top member, said aperture being in communication with a section of said connecting channel and providing an opening for said third push rod to deflect a portion of said flexible member over said connecting channel and thereby close off said connecting channel and thereby control flow of said biological specimen between said specimen conditioning chamber and said specimen enrichment chamber.

9. The biological specimen preparation system as claimed in claim 5, wherein said injector comprises first and second fluid couplers.

10. The biological specimen preparation system as claimed in claim 5, wherein said base member and said top member comprise injection molded pieces.

11. A method for preparing a biological specimen in a disposable specimen processing unit, said disposable specimen processing unit including an input port for coupling to a vial containing the biological specimen, and output port for coupling to a slide, said method comprising the steps of:

(a) injecting a portion of the biological specimen from said vial to a first specimen conditioning chamber in said disposable specimen processing unit;

(b) moving said biological specimen from said first specimen conditioning chamber to at least another specimen conditioning chamber in said disposable specimen processing unit for further conditioning;

(c) moving said biological specimen form said last specimen conditioning chamber to a specimen enrichment chamber in said disposable specimen processing unit;

(d) enriching said biological specimen in said specimen enrichment chamber by passing said biological specimen over a filter to remove contaminants from said biological specimen;

(e) moving said enriched biological specimen from said specimen enrichment chamber to said output port for deposition on the slide.

12. The method preparing a biological specimen in a disposable specimen processing unit as claimed in claim 11, further including the step of determining a cell density reading for the biological specimen at said specimen enrichment chamber and before moving said specimen to said output port.

13. The method for preparing a biological specimen in a disposable specimen processing unit as claimed in claim 11, further including the step of making an optical turbidity measurement before injecting a portion of said biological specimen into said first specimen conditioning chamber.

14. The method of preparing a biological specimen in a disposable specimen processing unit as claimed in claim 11, wherein cells in said enriched biological specimen are allowed to settle on the slide under the influence of gravity.

* * * * *